United States Patent
Shissler et al.

(10) Patent No.: US 9,295,797 B2
(45) Date of Patent: Mar. 29, 2016

(54) SYSTEM AND METHOD OF DETECTING AND RESPONDING TO SPONTANEOUS RESPIRATION SUBSEQUENT TO A RESPIRATORY EVENT

(75) Inventors: Andrew L. Shissler, Delmont, PA (US); Peter Douglas Hill, Monroeville, PA (US); Birpal Singh Sachdev, Delmont, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 457 days.

(21) Appl. No.: 13/821,310

(22) PCT Filed: Sep. 5, 2011

(86) PCT No.: PCT/IB2011/053875
§ 371 (c)(1),
(2), (4) Date: Apr. 16, 2013

(87) PCT Pub. No.: WO2012/032456
PCT Pub. Date: Mar. 15, 2012

(65) Prior Publication Data
US 2013/0199532 A1 Aug. 8, 2013

Related U.S. Application Data

(60) Provisional application No. 61/381,571, filed on Sep. 10, 2010.

(51) Int. Cl.
| | |
|---|---|
| A61M 16/06 | (2006.01) |
| A61B 5/08 | (2006.01) |
| A61M 16/00 | (2006.01) |
| A61M 16/08 | (2006.01) |

(52) U.S. Cl.
CPC .......... *A61M 16/0057* (2013.01); *A61B 5/0826* (2013.01); *A61M 16/00* (2013.01); *A61M 16/0666* (2013.01); *A61M 16/0875* (2013.01); *A61M 2016/0024* (2013.01); *A61M 2016/0036* (2013.01); *A61M 2205/505* (2013.01)

(58) Field of Classification Search
CPC ............ A61M 16/00; A61M 16/0009; A61M 16/0012; A61M 16/0051; A61M 16/0057; A61M 16/0081; F04D 25/166; F04D 29/052; G06F 19/3406
USPC ............. 128/204.18, 204.21, 204.22, 204.23, 128/204.24, 204.26
See application file for complete search history.

(56) References Cited

U.S. PATENT DOCUMENTS

| | | | |
|---|---|---|---|
| 5,385,142 A * | 1/1995 | Brady et al. ............. | 128/204.23 |
| 6,105,575 A | 8/2000 | Estes | |
| 6,158,432 A * | 12/2000 | Biondi et al. ............ | 128/204.21 |
| 6,349,724 B1 * | 2/2002 | Burton et al. ............ | 128/204.18 |
| 2005/0061319 A1 | 3/2005 | Hartley | |
| 2010/0018531 A1 | 1/2010 | Bassin | |
| 2010/0108064 A1 * | 5/2010 | Blackwell et al. ....... | 128/204.21 |
| 2011/0297156 A1 * | 12/2011 | Shelly et al. ............. | 128/204.23 |

FOREIGN PATENT DOCUMENTS

WO PCT/IB2010/050295 * 9/2010

* cited by examiner

*Primary Examiner* — Annette Dixon
(74) *Attorney, Agent, or Firm* — Michael W. Haas (57) ABSTRACT

A pressurized flow of breathable gas is delivered to the airway of a subject in accordance with a therapy regime. Responsive to the subject resuming respiration after a respiratory event, delivery of the pressurized flow of breathable gas is resumed at an inhalation in the therapy regime. As such, the therapy regime is effectively re-synchronized with the respiration of the subject subsequent to a respiratory event.

15 Claims, 5 Drawing Sheets

SYSTEM AND METHOD OF DETECTING AND RESPONDING TO SPONTANEOUS RESPIRATION SUBSEQUENT TO A RESPIRATORY EVENT

CROSS-REFERENCE TO RELATED APPLICATIONS

This patent application claims the priority benefit under 35 U.S.C. §371 of international patent application no. PCT/IB2011/053875, filed Sep. 5, 2011, which claims the priority benefit under 35 U.S.C. §119(e) of U.S. Provisional Application No. 61/381,571 filed on Sep. 10, 2010, the contents of which are herein incorporated by reference.

BACKGROUND OF THE INVENTION

1. Field of the Invention

The invention relates to the detection of respiratory events during positive airway pressure therapy for a subject, and the resumption of therapy subsequent to a respiratory event being spontaneously ended by the subject.

2. Description of the Related Art

Systems that provide positive pressure to the airway of a subject are known. Such systems may be used during sleep of the subject, and can be configured to detect respiratory events that disrupt respiration by the subject. In conventional systems, a test pulse of gas is transmitted to the airway of the subject during a respiratory event to determine more information about the respiratory event. In some cases, the transmission of the test pulse of gas inadvertently prompts the subject to resume spontaneous breathing, thereby bringing an end to the respiratory event.

SUMMARY OF THE INVENTION

One aspect of the invention relates to a system configured to detect spontaneous respiration by a subject after a respiratory event in which respiration by the subject was disrupted. In one embodiment, the system comprises a pressure generator, a sensor, and one or more processors. The pressure generator is configured to generate a pressurized flow of breathable gas for delivery to the airway of the subject. The sensor is configured to generate an output signal conveying information related to one or more fluid properties at or near the airway of the subject. The one or more processors are configured to execute one or more modules including an event detection module, a therapy module, and a respiration detection module. The event detection module is configured to detect, based on the output signal generated by the sensor, respiratory events of the subject. The therapy module is configured to control the pressure generator such that one or more fluid parameters of the pressurized flow of breathable gas are varied in accordance with a therapy regime, wherein the therapy module is further configured such that responsive to detection of a first respiratory event one or more fluid parameters of the pressurized flow of breathable gas are adjusted momentarily to provide a test pulse of gas to the airway of the subject that facilitates identification of an event type of the first respiratory event. The respiration detection module is configured to determine, based on the output signal generated by the sensor, whether the test pulse of gas has resulted in spontaneous respiration by the subject.

Another aspect of the invention relates to a method of detecting spontaneous respiration by a subject after a respiratory event in which respiration by the subject was disrupted. In one embodiment, the method comprises generating a pressurized flow of breathable gas for delivery to the airway of the subject such that one or more fluid parameters of the pressurized flow of breathable gas are varied in accordance with a therapy regime; generating an output signal conveying information related to one or more fluid properties at or near the airway of the subject; detecting, based on the output signal, a first respiratory event of the subject; responsive to detection of the first respiratory event, momentarily adjusting one or more fluid parameters of the pressurized flow of breathable gas to provide a test pulse of gas to the airway of the subject that facilitates identification of an event type of the first respiratory event; and determining, based on the output signal, whether the test pulse of gas has resulted in spontaneous respiration by the subject.

Yet another aspect of the invention relates to a system configured to detect spontaneous respiration by a subject after a respiratory event in which respiration by the subject was disrupted. In one embodiment, the system comprises means for generating a pressurized flow of breathable gas for delivery to the airway of the subject such that one or more fluid parameters of the pressurized flow of breathable gas are varied in accordance with a therapy regime; means for generating an output signal conveying information related to one or more fluid properties at or near the airway of the subject; means for detecting, based on the output signal, a first respiratory event of the subject; means for momentarily adjusting, responsive to detection of the first respiratory event, one or more fluid parameters of the pressurized flow of breathable gas to provide a test pulse of gas to the airway of the subject that facilitates identification of an event type of the first respiratory event; and means for determining, based on the output signal, whether the test pulse of gas has resulted in spontaneous respiration by the subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention.

DETAILED DESCRIPTION OF THE EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1:
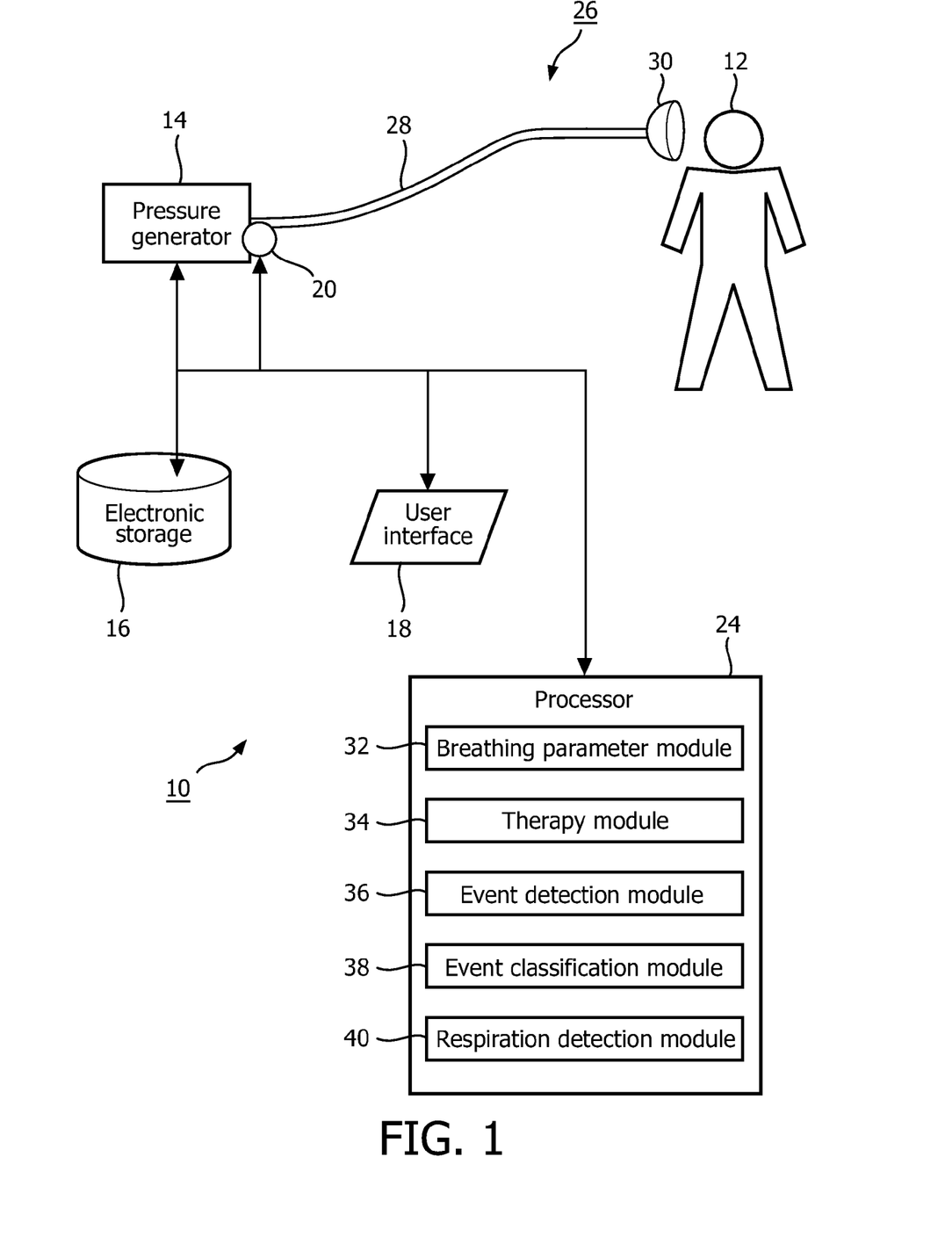
FIG. 1 illustrates a system configured to deliver a pressurized flow of breathable gas to the airway of a subject, in accordance with one or more embodiments of the invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein FIG. 1 illustrates a system 10 configured to deliver a pressurized flow of breathable gas to the airway of a subject 12 in accordance with a therapy regime. The pressurized flow of breathable gas may be delivered to the airway of subject 12 while subject 12 sleeps. The system 10 is further configured to monitor the respiration of subject 12. This may include one or more of determining one or more breathing parameters of the respiration of subject 12, detecting one or more respiratory events experienced by subject 12, determining an event type of one or more respiratory events experienced by subject 12, and/or other functionality. Responsive to subject 12 resuming respiration after a respiratory event, system 10 is configured to resume delivery of the pressurized flow of breathable gas at an inhalation in the therapy regime. As such, system 10 effectively re-synchronizes the therapy regime with the respiration of subject 12 subsequent to a respiratory event. In one embodiment, system 10 includes one or more of a pressure generator 14, electronic storage 16, a user interface 18, one or more sensors 20, a processor 24, and/or other components.

In one embodiment, pressure generator 14 is configured to generate a pressurized flow of breathable gas for delivery to the airway of subject 12. The pressure generator 14 may control one or more parameters of the pressurized flow of breathable gas (e.g., flow rate, pressure, volume, humidity, temperature, gas composition, etc.) for therapeutic purposes, or for other purposes. By way of non-limiting example, pressure generator 14 may be configured to control the pressure of the pressurized flow of breathable gas to provide pressure support to the airway of subject 12. The pressure generator 14 may include a positive pressure generator such as, for example, the device described in U.S. Pat. No. 6,105,575, hereby incorporated by reference in its entirety.

The pressurized flow of breathable gas is delivered to the airway of subject 12 via a subject interface 26. Subject interface 26 is configured to communicate the pressurized flow of breathable gas generated by pressure generator 14 to the airway of subject 12. As such, subject interface 26 includes a conduit 28 and an interface appliance 30. Conduit conveys the pressurized flow of breathable gas to interface appliance 30, and interface appliance 30 delivers the pressurized flow of breathable gas to the airway of subject 12. Some examples of interface appliance 30 may include, for example, a nasal cannula, a nasal mask, a nasal/oral mask, a full face mask, a total face mask, or other interface appliances that communication a flow of gas with an airway of a subject. The present invention is not limited to these examples, and contemplates delivery of the pressurized flow of breathable gas to subject 12 using any subject interface.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., generator 14, user interface 18, processor 24, etc.).

User interface 18 is configured to provide an interface between system 10 and one or more users (e.g., subject 12, a caregiver, a researcher, a therapy decision-maker, etc.) through which the users may provide information to and receive information from system 10. This enables data, cues, results, and/or instructions and any other communicable items, collectively referred to as "information," to be communicated between the users and one or more of pressure generator 14, electronic storage 16, and/or processor 24. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with generator 14.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

Sensors 20 are configured to generate one or more output signals conveying information related to one or more fluid parameters of the pressurized flow of breathable gas. The one or more parameters may include, for example, one or more of a flow rate, a volume, a pressure, a composition (e.g., concentration(s) of one or more constituents), humidity, temperature, acceleration, velocity, acoustics, changes in a parameter indicative of respiration, and/or other gas parameters. The sensors may include one or more sensors that measure such parameters directly (e.g., through fluid communication with the pressurized flow of breathable gas at pressure generator 14 or in subject interface 26). Sensors 20 may include one or more sensors that generate output signals related to one or more parameters of the pressurized flow of breathable gas indirectly. For example, one or more of sensors 20 may generate an output based on an operating parameter of pressure generator 14 (e.g., a valve driver or motor current, voltage, rotational velocity, and/or other operating parameters), and/or other sensors. Although sensors 20 are illustrated at a single location at or adjacent to pressure generator 14, this is not intended to be limiting. The sensors may include sensors disposed in a plurality of locations, such as for example, within pressure generator 14, within (or in communication with) conduit 28, within (or in communication with) interface appliance 30, and/or other locations.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination.

As is shown in FIG. 1, processor 24 may be configured to execute one or more computer program modules. The one or more computer program modules may include one or more of a breathing parameter module 32, a therapy module 34, an event detection module 36, an event classification module 38, a respiration detection module 40, and/or other modules. Processor 24 may be configured to execute modules 32, 34, 36, 38, and/or 40 by software; hardware; firmware; some combination of software, hardware, and/or firmware; and/or other mechanisms for configuring processing capabilities on processor 24.

It should be appreciated that although modules 32, 34, 36, 38, and 40 are illustrated in FIG. 1 as being co-located within a single processing unit, in implementations in which processor 24 includes multiple processing units, one or more of modules 32, 34, 36, 38, and/or 40 may be located remotely from the other modules. The description of the functionality provided by the different modules 32, 34, 36, 38, and/or 40 described below is for illustrative purposes, and is not intended to be limiting, as any of modules 32, 34, 36, 38, and/or 40 may provide more or less functionality than is described. For example, one or more of modules 32, 34, 36, 38, and/or 40 may be eliminated, and some or all of its functionality may be provided by other ones of modules 32, 34, 36, 38, and/or 40. As another example, processor 24 may be configured to execute one or more additional modules that may perform some or all of the functionality attributed below to one of modules 32, 34, 36, 38, and/or 40.

The breathing parameter module 32 is configured to determine one or breathing parameters of the respiration of subject 12. Breathing parameter module 32 determines the one or more breathing parameters of the respiration of subject 12 based on the output signals generated by sensors 20. The one or more breathing parameters determined by breathing parameter module 32 may include one or more of tidal volume, peak flow, respiration rate, timing of breathing transitions (e.g., from inhalation to exhalation, from exhalation to inhalation, and/or other transitions), flow contour, flow limitation, and/or other breathing parameters.

Therapy module 34 is configured to control pressure generator 14 to adjust the parameters of the pressurized flow of breathable gas in accordance with a therapy regime. A non-limiting example of one such regime is Continuous Positive Airway Pressure (CPAP). CPAP has been used for many years and has proven to be helpful in promoting regular breathing. Another therapy regime for generating the pressurized flow of breathable gas is bi-level positive air pressure mode (BI-PAP®). In bi-level positive air pressure mode, two levels of positive air pressure (HI and LO) are supplied to a patient. Other modes of generating the pressurized flow of breathable gas are contemplated. Generally, the timing of the HI and LO levels of pressure are controlled such that the HI level of positive air pressure is delivered to subject 12 during inhalation (known as Inspiratory Positive Airway Pressure or IPAP) and the LO level of pressure is delivered to subject 12 during exhalation (known as Expiratory Positive Airway Pressure or EPAP). The timing of adjustments to the parameters of the pressurized flow of breathable gas in accordance with a therapy regime may be determined by therapy module 34 based on the one or more breathing parameters determined by breathing parameter module 32. The level(s) of flow rate, pressure, and/or other fluid parameters dictated by a given therapy regime may be predetermined for the given therapy regime, determined based on user preferences or settings, determined based on one or more breathing parameters determined by breathing parameter module 32, and/or otherwise determined.

Event detection module 36 is configured to detect respiratory events experienced by subject 12. Such respiratory events include events that disrupt respiration by subject 12. For example, such respiratory events may include one or more of obstructive apneas, central apneas, glottal closures, and/or other respiratory events. Event detection module 36 detects such respiratory events based on the output signals generated by sensors 20. For example, by monitoring one or more of flow rate, pressure, instantaneous tidal volume, and/or other fluid parameters at or near the airway of subject 12 (e.g., within subject interface 26 and/or pressure generator 14), event detection module 36 can detect disruptions of the respiration of subject 12 indicative of respiratory events.

Therapy module 34 is further configured such that responsive to detection by event detection module 36 of a respiratory event, one or more fluid parameters of the pressurized flow of breathable gas are adjusted momentarily to provide a test pulse of gas to the airway of the subject. The test pulse of gas facilitates identification of an event type of the first respiratory event. More particularly, the response of the subject 12 to the test pulse of gas is indicative of an event type of the first respiratory event. The test pulse of gas does not provide enough mechanical support/pressure to the airway of subject 12 to physically assist subject 12 in overcoming a respiratory event. Instead, it is a mere diagnostic artifact introduced into the pressurized flow of breathable gas to facilitate determination of event type. The pressure, flow rate, and/or duration of the test pulse of gas may be insufficient to provide mechanical support/pressure sufficient to overcome a respiratory event. By way of non-limiting example, the test pulse of gas may be about 2 cmH2O and/or some other pressure, may last about 1 second, about 1.2 seconds, about 1.5 seconds, and/or other durations, and/or have other parameters.

Event classification module 38 is configured to determine event types of respiratory events detected by event detection module 36. The event classification module is configured to determine the event types based on the output signal generated by sensors 20 during delivery of the test pulse of gas. The event types may include one or more of an obstructive apnea, a central apnea, and/or other respiratory events that disrupt respiration of subject 12.

Figure 2:
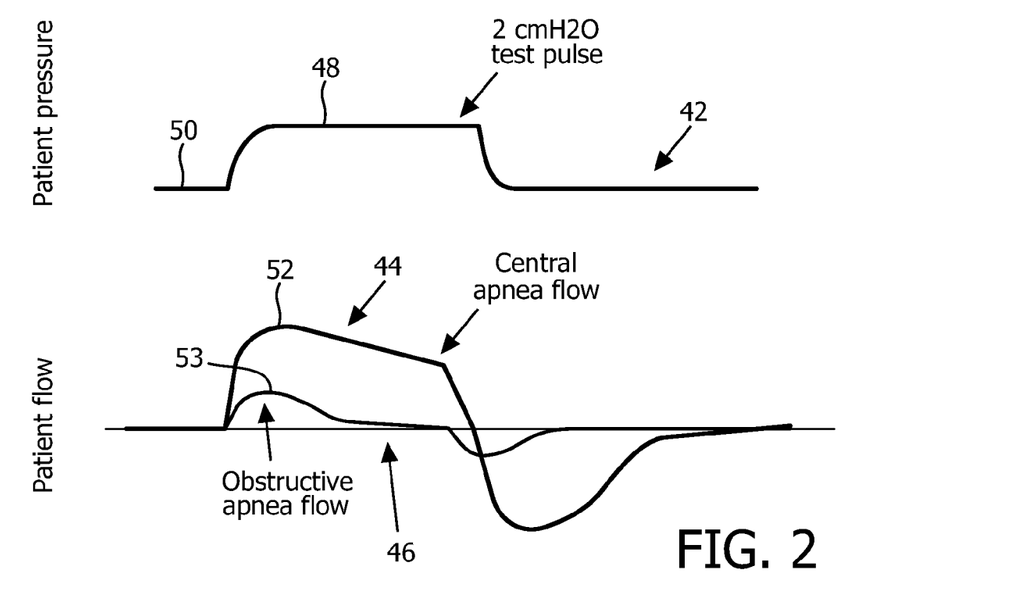
FIG. 2 depicts plots of pressure and flow rate illustrating delivery of a test pulse of gas to the airway of a subject, according to one or more embodiments of the invention.

By way of illustration, FIG. 2 depicts plots representing delivery of a test pulse of gas to the airway of a subject, and how the reaction of the subject to the test pulse indicates a respiratory event type. The plots comprise a pressure plot 42 of pressure at or near the airway of the subject, a first flow plot 44 of flow rate at or near the airway of the subject, and a second flow plot 46 of flow rate at or near the airway of the subject. Plots 42, 44, and/or 46 may represent measurements taken at or near the airway of the subject and/or estimates made from measurements taken further away from the airway of the subject (e.g., to account for leak and/or loss). Plot 42 shows how delivery of the test pulse of gas results in a momentary elevation 48 from a baseline pressure level 50 (e.g., the normal EPAP level). First flow plot 44 shows the response of the subject experiencing a central apnea. Because the airway of the subject is unblocked during the central apnea, the momentary elevation in pressure 48 results in a corresponding elevation in flow 52 at or near the airway of the subject. The second flow plot 46 shows the response of the subject experiencing an obstructive apnea. Because the airway of the subject is blocked during the obstructive apnea, an elevation in flow 53 corresponding to the momentary elevation in pressure 48 has a significantly lower magnitude than elevation in flow 52.

Returning to FIG. 1, upon determining an event type of a respiratory event, event classification module 38 may store information about the respiratory event (e.g., to electronic storage 16). The information stored may be used to adjust future therapy for subject 12, for diagnostic purposes, for reference by a clinician advising or treating subject 12, and/or for other purposes.

In some cases, application of a test pulse of gas to the airway of subject 12 may cause subject 12 to renew spontaneous respiration. Although the test pulse of gas is not large/strong/long enough to provide mechanical support or pressure sufficient to overcome a respiratory event, the test pulse of gas may elicit a response from subject 12 that results in renewed and/or strengthened respiratory effort. In such cases, renewed respiration subsequent to a respiratory event will likely begin with a new inspiration. Conventional systems typically do not attempt to detect resumption of respiration responsive to a test pulse. As such, if a test pulse does prompt subject 12 to resume spontaneous respiration, the newly resumed respiration may be out of synch with the therapy regime. Re-synchronization of the therapy regime to the respiration of subject 12 (and/or synchronization of the respiration of subject 12 to the therapy regime) may take some time, and may cause subject 12 to awaken.

The respiration detection module 40 is configured to determine whether a test pulse of gas has resulted in spontaneous respiration by subject 12. This determination is made based on the output signal generated by subject 12. For example, respiration detection module 40 may monitor flow rate at or near the airway of subject 12 to determine whether a test pulse of gas has resulted in spontaneous respiration by subject 12. This determination may include arming a trigger comprising a trigger condition (e.g., breach of a flow rate threshold) subsequent to initiation of a test pulse of gas, and then determining whether spontaneous respiration has resumed based on whether the trigger is satisfied.

The arming of the trigger by respiration detection module 40 is performed responsive to one or more arming conditions. The arming condition(s) used in a particular instance may be based an identified event type of the respiratory event (e.g., as identified by event classification module 38). By way of non-limiting example, the arming conditions may include one or more of a time elapsed from the initiation of a test pulse of gas, a decrease in flow rate at or near the airway of subject 12 of a threshold amount from a maximum flow rate during a test pulse of gas, and/or other arming conditions.

Once the trigger is armed by respiration detection module 40 responsive to detection of one or more arming conditions, respiration detection module 40 is configured to detect satisfaction of one or more trigger conditions. The one or more trigger conditions may include flow rate rising to a threshold level (indicating spontaneous inhalation by subject 12), a rise in flow rate of a threshold amount (indicating spontaneous inhalation by subject 12), and/or other trigger conditions. Upon detection of the one or more trigger conditions, respiration detection module 40 determines that subject 12 has initiated spontaneous respiration responsive to the test pulse of gas.

Figure 3:
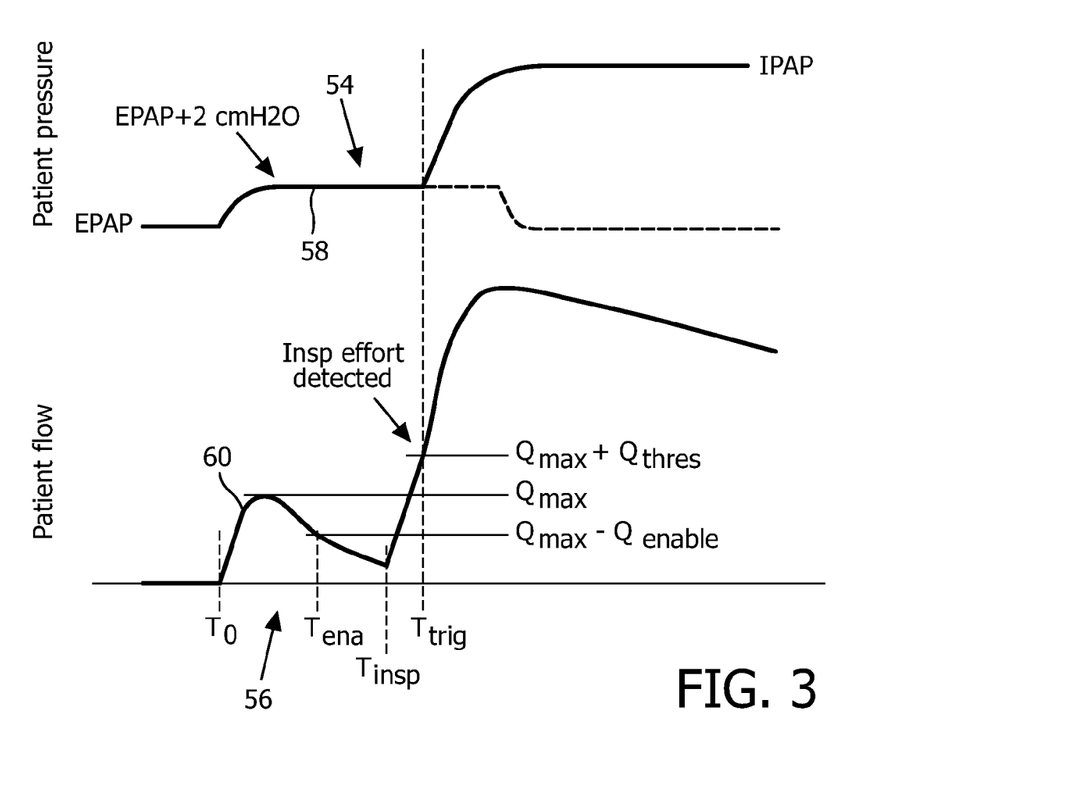
FIG. 3 depicts plots of pressure and flow rate illustrating the arming of a trigger and the satisfaction of the trigger, in accordance with one or more embodiments of the invention.

By way of illustration, FIG. 3 shows a pressure plot 54 and a flow rate plot 56 that depict the arming of a trigger and detection of spontaneous respiration of a subject based on the armed trigger. In particular, in the embodiment illustrated in FIG. 3, the subject is experiencing a central apnea (or related respiratory event). Prior to an initiation time (T0), a pressurized flow of breathable gas is delivered to the subject at an EPAP level. At the initiation time (T0) a respiratory event is detected and a test pulse of gas transmitted to the subject results in a rise in pressure 58. A rise in flow rate 60 caused by the test pulse of gas occurs to a maximum flow (Qmax), followed by a tapering off of the flow rate indicative of a central apnea. As the flow rate tapers off from the maximum flow (Qmax), the decrease reaches or exceeds a threshold drop amount (Qena). This occurs in FIG. 3 at an arm time (Tena). Detection of the reaching and/or exceeding of this threshold drop amount results in a trigger being armed at arm time (Tena).

The arming of the trigger results in monitoring the flow rate for satisfaction of a trigger condition. The trigger condition may be satisfied if the flow rate rises above a threshold level. The threshold may be a predetermined level, may be determined based on user selection (e.g., a setting or preference), may be determined based on a measured flow rate (e.g., some measured flow rate plus a threshold amount), and/or otherwise determined. In the embodiment shown in FIG. 3, the threshold level is determined as the maximum flow rate (Qmax) plus a threshold amount (Qthres).

At a time of inspiration (Tinsp), the subject is prompted by the test pulse of gas to begin breathing spontaneously. This initiation of spontaneous respiration results in an inspiration by the subject that commences at the time of inspiration (Tinsp), shown in flow rate plot 56 as an increase in flow rate. As the flow rate during this initial inspiration increases, the flow rate is monitored to determine if the flow rate has breached the threshold amount of the trigger condition (Qmax+Qthres). Responsive to the flow rate breaching this threshold amount at a trigger time (Ttrig), a determination is made that the subject has responded to the test pulse of gas by spontaneously resuming breathing.

Figure 4:
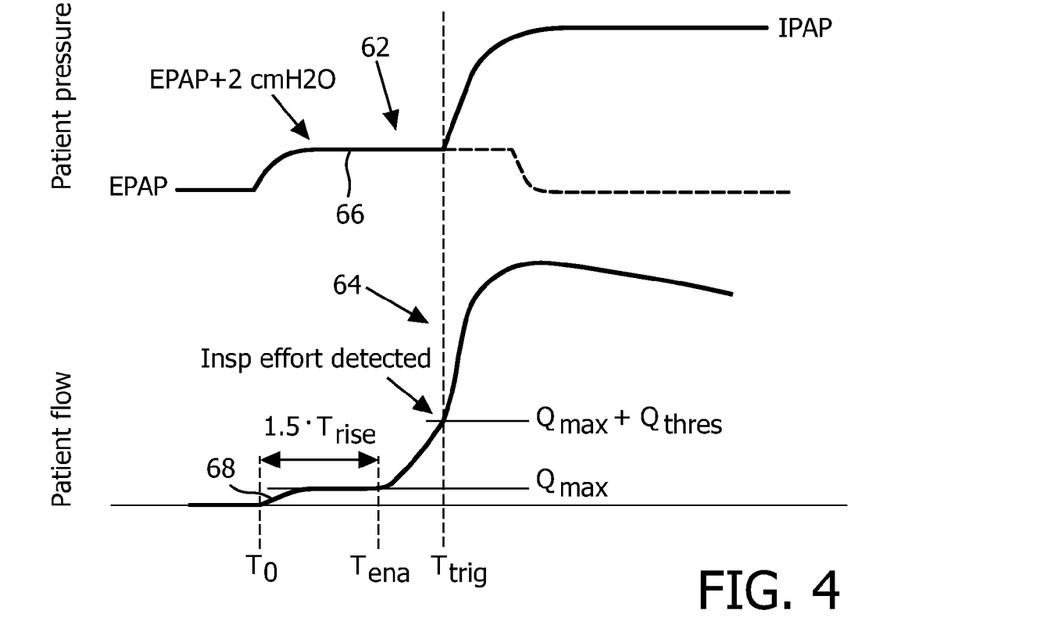
FIG. 4 depicts plots of pressure and flow rate illustrating the arming of a trigger and the satisfaction of the trigger, in accordance with one or more embodiments of the invention.

By way of further illustration, FIG. 4 shows a pressure plot 62 and a flow rate plot 64 that depict the arming of a trigger and detection of spontaneous respiration of a subject based on the armed trigger. Specifically, in the embodiment illustrated in FIG. 4, the subject is experiencing an obstructive apnea (or related respiratory event). Prior to an initiation time (T0), a pressurized flow of breathable gas is delivered to the subject at an EPAP level. At the initiation time (T0) a respiratory event is detected and a test pulse of gas transmitted to the subject results in a rise in pressure 66. A rise in flow rate 68 caused by the test pulse of gas occurs to a maximum flow (Qmax) at which point flow rate plateaus, indicative of an obstructive apnea. At an amount of time subsequent to the initiation time (T0), a trigger is armed. This occurs in FIG. 4 at an arm time (Tena). In the embodiment shown in FIG. 4, the amount of time from the initiation time (T0) to arming of the trigger at the arm time (Tena) is determined as 1.5 times the rise time, or the time it takes for the flow rate to increase to a maximum flow (Qmax) from the flow rate at the initiation time (Qmax).

The arming of the trigger results in monitoring the flow rate for satisfaction of a trigger condition. In the embodiment shown in FIG. 4, the trigger is satisfied if the flow rate increases to or above a threshold amount. The threshold amount is determined as the maximum flow rate (Qmax) plus a threshold amount (Qthres).

Figure 5:
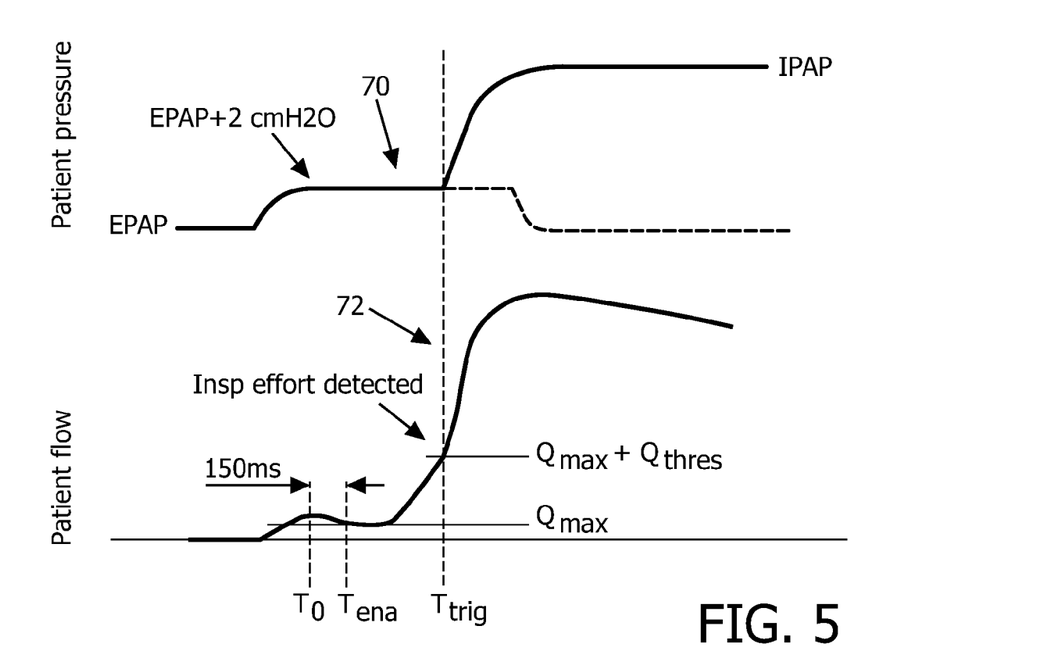
FIG. 5 depicts plots of pressure and flow rate illustrating the arming of a trigger and the satisfaction of the trigger, in accordance with one or more embodiments of the invention.

By way of still further illustration with respect to arming a trigger, FIG. 5 shows a pressure plot 70 and a flow rate plot 72. The plots 70 and 72 correspond to an embodiment similar to the one shown in FIG. 4 and described above. However, in the embodiment shown in FIG. 5, the arming condition includes the passing of a threshold amount of time from the flow rate at or near the airway of a subject reaching a maximum flow rate (Qmax). The amount of time may be predetermined, may be determined based on user selection (e.g., setting or preference), and/or may otherwise be determined. In one embodiment, the amount of time is about 150 ms.

Returning to FIG. 1, responsive to respiration detection module 40 arming the trigger and then determining subject 12 has resumed spontaneous respiration, therapy module 34 is configured to control pressure generator 14 to resume the therapy regime at an inspiration. This will cause the therapy regime to be immediately re-synchronized with the respiration of subject 12 without a period of desynchronicity that may result in waking subject 12, requiring increased respiratory effort from subject 12, and/or issues associated with the period of desynchronicity.

Referring back to FIGS. 3-5, pressure plots 54, 62, and 70 show how pressure of the pressurized flow of breathable gas is adjusted responsive to satisfaction of the trigger at the trigger time (Ttrig). Specifically, in the embodiments shown, the pressure of the pressurized flow of breathable gas is adjusted from the EPAP level to the IPAP level at the trigger time (Ttrig).

Figure 6:
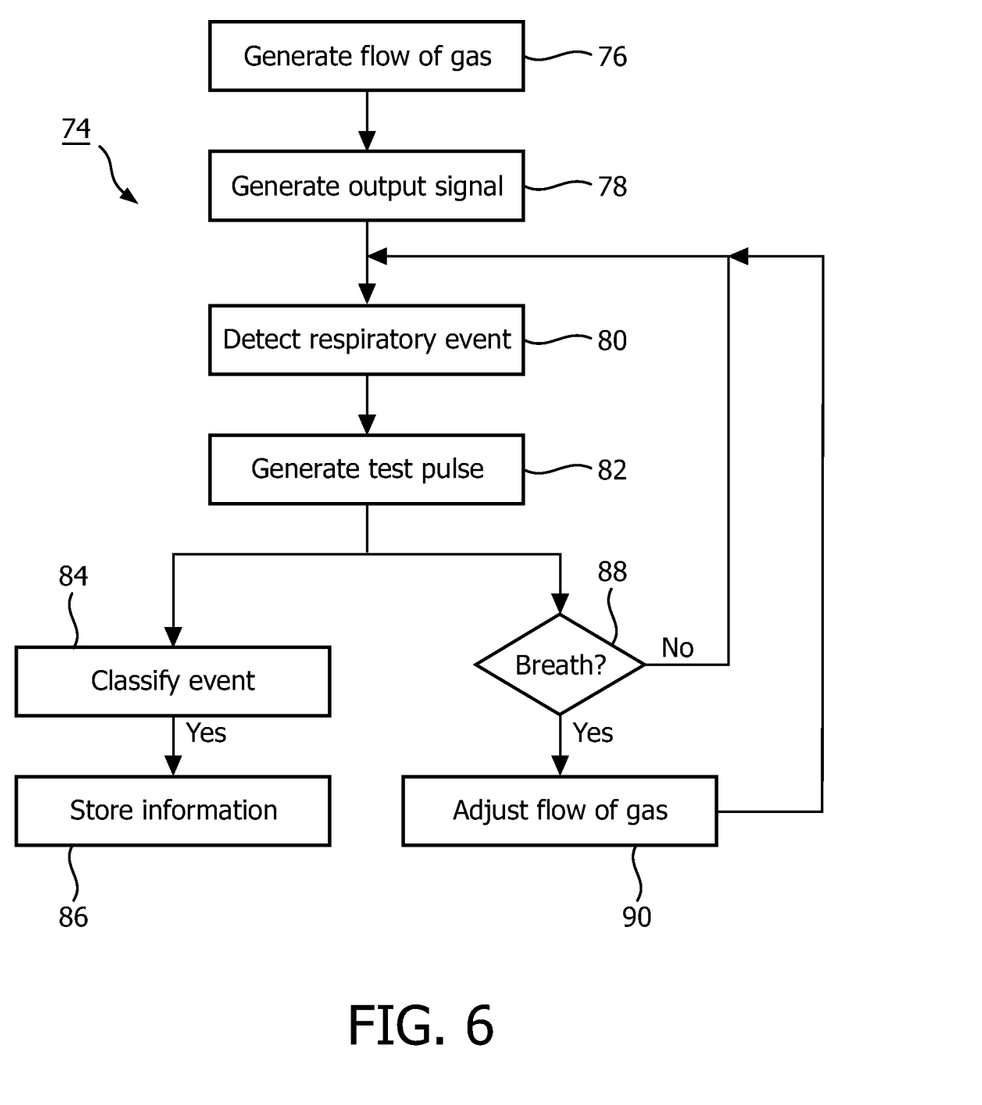
FIG. 6 illustrates a method of detecting spontaneous respiration by a subject after a respiratory event in which respiration by the subject was disrupted, according to one or more embodiments of the invention.

FIG. 6 illustrates a method 74 of detecting spontaneous respiration by a subject after a respiratory event in which respiration by the subject was disrupted. The operations of method 74 presented below are intended to be illustrative. In some embodiments, method 74 may be accomplished with one or more additional operations not described, and/or without one or more of the operations discussed. Additionally, the order in which the operations of method 74 are illustrated in FIG. 6 and described below is not intended to be limiting.

In some embodiments, method 74 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 74 in response to instructions stored electronically on an electronic storage medium. The one or more processing devices may include one or more devices configured through hardware, firmware, and/or software to be specifically designed for execution of one or more of the operations of method 74.

At an operation 76, a pressurized flow of breathable gas is generated for delivery to the airway of the subject. The pressurized flow of breathable gas is generated having one or more fluid parameters varied in accordance with a therapy regime. In one embodiment, operation 76 is performed by a pressure generator similar to or the same as pressure generator 14 (shown in FIG. 1 and described above) under the control of a therapy module similar to or the same as therapy module 34 (shown in FIG. 1 and described above).

At an operation 78, an output signal is generated conveying information related to one or more fluid parameters at or near the airway of the subject. In one embodiment, operation 78 is performed by one or more sensors similar to or the same as sensors 20 (shown in FIG. 1 and described above).

At an operation 80, a respiratory event disrupting the respiration of the subject is detected. The respiratory event may include an obstructive or central apnea, hypopnea, glottal closure, and/or other respiratory events. This detection is based on the output signal generated at operation 78. In one embodiment, operation 80 is performed by an event detection module similar to or the same as event detection module 36 (shown in FIG. 1 and described above).

At an operation 82, one or more fluid parameters of the pressurized flow of breathable gas are adjusted to provide a test pulse of gas to the airway of the subject. The test pulse of gas facilitating classification of the respiratory event. The test pulse of gas does not have sufficient pressure/strength/duration to mechanically overcome the respiratory event. In one embodiment, operation 82 is performed by a pressure generator similar to or the same as pressure generator 14 (shown in FIG. 1 and described above) under the control of a therapy module similar to or the same as therapy module 34 (shown in FIG. 1 and described above).

At an operation 84, the respiratory event is classified. This includes determining an event type of the respiratory event. The event type may include one or more of a central apnea, an obstructive apnea, hypopnea, glottal closure, and/or other event types. The determination of event type is based on the output signal generated at operation 78 during delivery of the test pulse of gas to the subject at operation 82. In one embodiment, operation 84 is performed by an event classification module similar to or the same as event classification module 38 (shown in FIG. 1 and described above).

At an operation 86, information determined at operation 84 is stored to electronic storage. In one embodiment, operation 84 includes storage to electronic storage similar to or the same as electronic storage 16.

At an operation 88, responsive to delivery of the test pulse of gas at operation 82, a determination is made as to whether the test pulse of gas has prompted spontaneous respiration by the subject. Responsive to a determination that the test pulse of gas has not prompted spontaneous respiration by the subject, method 74 returns to monitoring for respiratory events. Responsive to a determination that the test pulse of gas has prompted spontaneous respiration by the subject, method 74 proceeds to an operation 90. In one embodiment, operation 88 is performed by a respiration detection module similar to or the same as respiration detection module 40 (shown in FIG. 1 and described above).

At operation 90, the therapy regime is resumed at an inspiration. In one embodiment, operation 90 is performed by a pressure generator similar to or the same as pressure generator 14 (shown in FIG. 1 and described above) under the control of a therapy module similar to or the same as therapy module 34 (shown in FIG. 1 and described above).

Figure 7:
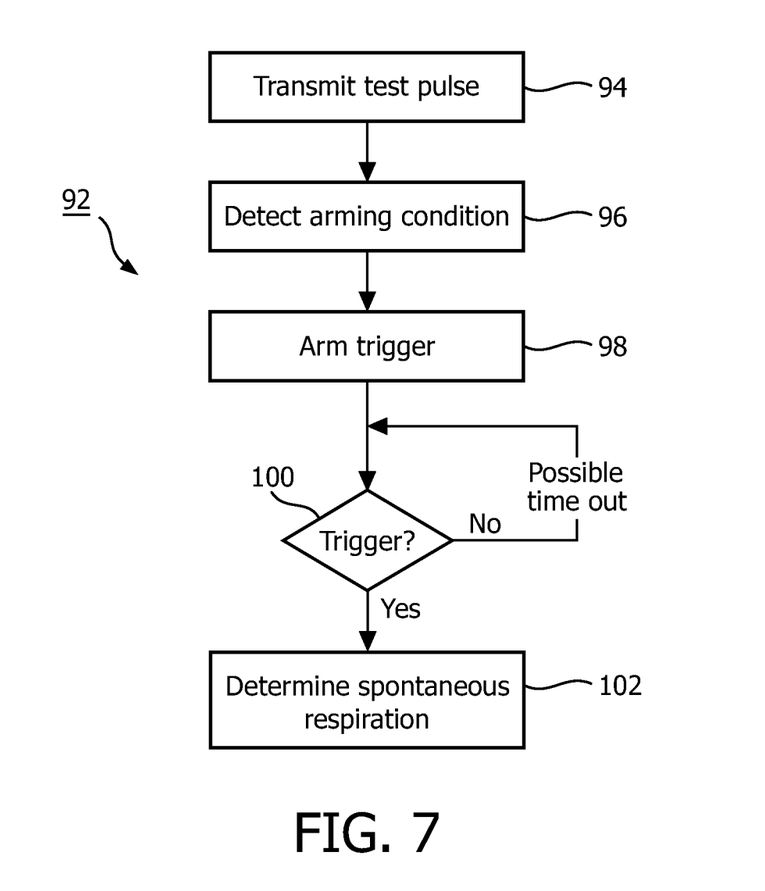
FIG. 7 illustrate a method of determining whether a test pulse of gas has prompted a subject to resume spontaneous respiration, according to one or more embodiments of the invention.

FIG. 7 illustrates a method 92 of determining whether a test pulse of gas has prompted a subject to resume spontaneous respiration. The operations of method 92 presented below are intended to be illustrative. In some embodiments, method 92 may be accomplished with one or more additional operations not described, and/or without one or more of the operations discussed. Additionally, the order in which the operations of method 92 are illustrated in FIG. 7 and described below is not intended to be limiting. In one embodiment, method 92 is implemented as operation 88 in method 74 (shown in FIG. 6 and described above). This does not limit the scope of the disclosure, as method 92 may be usable in a variety of other contexts.

In some embodiments, method 92 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 92 in response to instructions stored electronically on an electronic storage medium. The one or more processing devices may include one or more devices configured through hardware, firmware, and/or software to be specifically designed for execution of one or more of the operations of method 92.

At an operation 94, the test pulse of gas is generated for delivery to the airway of the subject. The test pulse of gas facilitates classification of a respiratory event being experienced by the subject. In one embodiment, operation 94 is performed by a pressure generator similar to or the same as pressure generator 14 (shown in FIG. 1 and described above) under the control of a therapy module similar to or the same as therapy module 34 (shown in FIG. 1 and described above).

At an operation 96, an arming condition is detected. The arming condition may include flow rate at or near the airway of the subject breaching a threshold level, passage of an amount of time, and/or other conditions. In one embodiment, operation 96 is performed by a respiration detection module similar to or the same as respiration detection module 40 (shown in FIG. 1 and described above).

At an operation 98, responsive to detection of the arming condition being satisfied at operation 96, a trigger is armed. The trigger may be satisfied through the satisfaction of a trigger condition. In one embodiment, operation 98 is performed by a respiration detection module similar to or the same as respiration detection module 40 (shown in FIG. 1 and described above).

At an operation 100, the armed trigger is monitored to determine if the trigger condition has been satisfied. This monitoring may be ongoing for some timeout period, or for some other period of time. Satisfaction of the trigger condition may require the flow rate at or near the airway of the subject to breach a threshold level. Responsive to the trigger condition has been satisfied, method 92 proceeds to an operation 102. In one embodiment, operation 100 is performed by a respiration detection module similar to or the same as respiration detection module 40 (shown in FIG. 1 and described above).

At an operation 102, a determination is made that the subject has resumed spontaneous respiration. In one embodiment, operation 102 is performed by a respiration detection module similar to or the same as respiration detection module 40 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to detect spontaneous respiration by a subject after respiratory events in which respiration by the subject was disrupted, the system comprising:
    (a) a pressure generator configured to generate a pressurized flow of breathable gas for delivery to the airway of a subject;
    (b) a sensor configured to generate an output signal conveying information related to one or more fluid properties at or near the airway of the subject; and
    (c) one or more hardware processors configured by machine-readable instructions to:
        (1) detect, based on the output signal generated by the sensor, the respiratory events of the subject,
        (2) control the pressure generator such that one or more fluid parameters of the pressurized flow of breathable gas are varied in accordance with a therapy regime, the one or more fluid parameters including an inspiratory positive airway pressure, wherein, responsive to detection of a first respiratory event, one or more fluid parameters of the pressurized flow of breathable gas are adjusted momentarily to provide a test pulse of gas to the airway of the subject that facilitates identification of an event type of the first respiratory event, the test pulse having a pressure that is less than the inspiratory positive airway pressure;
        (3) determine, based on the output signal generated by the sensor, whether there is spontaneous respiration by the subject responsive to the test pulse; and
        (4) responsive to determining that there is spontaneous respiration responsive to the test pulse, synchronize the therapy regime with spontaneous respiration that is responsive to the test pulse.

2. The system of claim 1, wherein the one or more hardware processors are further configured such that responsive to determining that there is spontaneous respiration by the subject, the therapy regime is synchronized at an inspiration by the subject, the determining that there is spontaneous respiration comprising:

arming a spontaneous respiration trigger responsive to providing the test pulse, the trigger comprising one or more trigger conditions related to the one or more fluid properties at or near the airway of the subject after the test pulse is provided; and determining that there is spontaneous respiration responsive to one or more of the one or more fluid properties at or near the airway of the subject after the test pulse is delivered satisfying one or more of the one or more synchronization conditions.

3. The system of claim 1, wherein the one or more hardware processors are further configured to determine, based on the output signal generated by the sensor conveying information related to the one or more fluid parameters at or near the airway of the subject during delivery of the test pulse of gas, an event type of the first respiratory event.

4. The system of claim 1, wherein the one or more hardware processors are further configured such that responsive to determination that the test pulse of gas has not resulted in spontaneous respiration byte subject, one or more fluid parameters of the pressurized flow of breathable gas are adjusted to aid the subject in overcoming the event.

5. The system of claim 1, wherein the one or more hardware processors are configured such that the respiratory events are apneas.

6. A method of detecting spontaneous respiration by a subject after a respiratory event in which respiration by the subject was disrupted, the method comprising:

generating a pressurized flow of breathable gas for delivery to the airway of the subject such that one or more fluid parameters of the pressurized flow of breathable gas are varied in accordance with a therapy regime, the one or more fluid parameters including an inspiratory positive airway pressure;

generating an output signal conveying information related to one or more fluid properties at or near the airway of the subject;

detecting, based on the output signal, a first respiratory event of the subject;

responsive to detection of the first respiratory event, momentarily adjusting one or more fluid parameters of the pressurized flow of breathable gas to provide a test pulse of gas to the airway of the subject that facilitates identification of an event type of the first respiratory event, the test pulse having a pressure that is less than the inspiratory positive airway pressure;

determining, based on the output signal, whether there is spontaneous respiration by the subject responsive to the test pulse; and responsive to determining that there is spontaneous respiration responsive to the test pulse, synchronizing the therapy regime with spontaneous respiration that is responsive to the test pulse.

7. The method of claim 6, further comprising, responsive to the determination that there is spontaneous respiration by the subject, synchronizing the therapy regime at an inspiration by the subject, wherein the determining that there is spontaneous respiration comprises:

arming a spontaneous respiration trigger responsive to providing the test pulse, the trigger comprising one or more trigger conditions related to the one or more fluid properties at or near the airway of the subject after the test pulse is provided; and determining that there is spontaneous respiration responsive to one or more of the one or more fluid properties at or near the airway of the subject after the test pulse is delivered satisfying one ore more of the one or more synchronization conditions.

8. The method of claim 6, further comprising determining, based on the output signal conveying information related to the one or more fluid parameters at or near the airway of the subject during delivery of the test pulse of gas, an event type of the first respiratory event.

9. The method of claim 6, further comprising, responsive to determination that the test pulse of gas has not resulted in spontaneous respiration by the subject, adjusting one or more fluid parameters of the pressurized flow of breathable gas to aid the subject in overcoming the first respiratory event.

10. The method of claim 6, wherein the first respiratory event is an apnea.

11. A system configured to detect spontaneous respiration by a subject after a respiratory event in which respiration by the subject was disrupted, the system comprising:

means for generating a pressurized flow of breathable gas for delivery to the airway of the subject such that one or more fluid parameters of the pressurized flow of breathable gas are varied in accordance with a therapy regime, the one or more fluid parameters including an inspiratory positive airway pressure;

means for generating an output signal conveying information related to one or more fluid properties at or near the airway of the subject;

means for detecting, based on the output signal, a first respiratory event of the subject;

means for momentarily adjusting, responsive to detection of the first respiratory event, one or more fluid parameters of the pressurized flow of breathable gas to provide a test pulse of gas to the airway of the subject that facilitates identification of an event type of the first respiratory event, the test pulse having a pressure that is less than the inspiratory positive airway pressure;

means for determining, based on the output signal, whether there is spontaneous respiration by the subject responsive to the test pulse; and means for synchronizing, responsive to determining that there is spontaneous respiration responsive to the test pulse, the therapy regime with spontaneous respiration that is responsive to the test pulse.

12. The system of claim 11, wherein the means for synchronizing is configured to synchronize the therapy regime with the spontaneous respiration of the subject at an inspiration by the subject, and wherein determining whether there is spontaneous respiration comprises:

arming a spontaneous respiration trigger responsive to providing the test pulse, the trigger comprising one or more trigger conditions related to the one or more of fluid properties at or near the airway of the subject after the test pulse is provided; and determining that there is spontaneous respiration responsive to one or more of the one or more fluid properties at or near the airway of the subject after the test pulse is delivered satisfying one or more of the one or more synchronization conditions.

13. The system of claim 11, further comprising means for determining, based on the output signal conveying information related to the one or more fluid parameters at or near the airway of the subject during delivery of the test pulse of gas, an event type of the first respiratory event.

14. The system of claim 11, further comprising means for adjusting, responsive to determination that the test pulse of gas has not resulted in spontaneous respiration by the subject, one or more fluid parameters of the pressurized flow of breathable gas to aid the subject in overcoming the first respiratory event.

15. The system of claim 11, wherein the first respiratory event is an apnea.

* * * * *